United States Patent
Aalders et al.

(10) Patent No.: US 10,222,324 B1
(45) Date of Patent: Mar. 5, 2019

(54) DRIED BLOOD SAMPLE ANALYSIS

(71) Applicant: UNIVERSITEIT GENT, Ghent (BE)

(72) Inventors: Maurice Aalders, Amsterdam (NL);
Leah Wilk, Amsterdam (NL); Sara Capiau, Steenhuize-Wijnhulze (BE);
Christophe Stove, Merelbeke (BE)

(73) Assignee: Universiteit Gent, Ghent (BE)

( * ) Notice: Subject to any disclaimer, the term of this patent is extended or adjusted under 35 U.S.C. 154(b) by 0 days.

(21) Appl. No.: 15/763,179

(22) PCT Filed: Oct. 5, 2016

(86) PCT No.: PCT/EP2016/073741
§ 371 (c)(1),
(2) Date: Jun. 29, 2018

(87) PCT Pub. No.: WO2017/060271
PCT Pub. Date: Apr. 13, 2017

(30) Foreign Application Priority Data

Oct. 5, 2015 (EP) .................................... 15188354

(51) Int. Cl.
*G01N 33/48* (2006.01)
*G01N 21/31* (2006.01)
(Continued)

(52) U.S. Cl.
CPC ......... *G01N 21/31* (2013.01); *G01N 21/4738* (2013.01); *G01N 33/49* (2013.01); *G01N 2021/3129* (2013.01)

(58) Field of Classification Search
CPC .... G01N 21/251; G01N 21/314; G01N 21/29; G01N 21/3151; G01N 33/49
(Continued)

(56) References Cited

U.S. PATENT DOCUMENTS

| 5,759,774 A | 6/1998 | Hackett et al. |
| 6,040,135 A | 3/2000 | Tyrrell |

(Continued)

FOREIGN PATENT DOCUMENTS

| WO | 2003052390 A1 | 6/2003 |
| WO | 2011068998 A2 | 6/2011 |
| WO | 2014004935 A2 | 1/2014 |

OTHER PUBLICATIONS

PCT International Search Report and Written Opinion dated Feb. 6, 2017 for PCT International Patent Application No. PCT/EP2016/073741, 14 pages.
(Continued)

*Primary Examiner* — Md M Rahman
(74) *Attorney, Agent, or Firm* — Amster, Rothstein & Ebenstein LLP

(57) ABSTRACT

A non-destructive method of estimating hematocrit (Hct) of whole blood from a dried blood sample prepared from the whole blood, the method comprising: a) determining the amount of hemoglobin derivatives comprising oxyhemoglobin, met-hemoglobin and hemichrome (total hemoglobin) in a dried blood sample, wherein the sum of the amounts of the hemoglobin derivatives remains constant in the dried blood sample in function of time, and b) estimating the hematocrit from the sum of the amounts of the hemoglobin derivatives, wherein the hematocrit is estimated using a calibration curve providing a correlation between hematocrit and the amount of the hemoglobin derivatives in a dried blood sample. The amount of the hemoglobin derivatives is preferably determined by measuring the reflectance, absorbance, or transmittance of the dried blood sample at the quasi-isosbestic point of the hemoglobin derivatives about 589 nm or at multiple wavelengths within the range of 450 to 750 nm.

21 Claims, 12 Drawing Sheets

(51) Int. Cl.
*G01N 21/47* (2006.01)
*G01N 33/49* (2006.01)

(58) Field of Classification Search
USPC .......................................................... 356/40
See application file for complete search history.

(56) References Cited

U.S. PATENT DOCUMENTS

| 6,187,531 B1 | 2/2001 | Tyrrell |
| 2005/0287678 A1 | 12/2005 | Morrison |
| 2013/0043374 A1 | 2/2013 | Morrison |
| 2015/0108344 A1 | 4/2015 | Amderspm |

OTHER PUBLICATIONS

PCT International Preliminary Report on Patentability dated Sep. 18, 2017 for PCT International Patent Application No. PCT/EP2016/073741, 21 pages.

Capiau S et al: "A Novel, Nondestructive, Dried Blood Spot-Based Hematocrit Prediction Method Using Noncontact Diffuse Reflectance Spectroscopy", Analytical Chemistry, vol. 88, No. 12, Jun. 21, 2016 (Jun. 21, 2016), pp. 6538-6546.

Bremmer R H et al : "Age estimation of blood stains by hemoglobin derivative determination using reflectance spectroscopy", Forensic Science International, vol. 206, No. 1-3, Mar. 20, 2011 (Mar. 20, 2011), pp. 166-171.

(Hb measurement on Cobas 8000)

DRIED BLOOD SAMPLE ANALYSIS

CROSS-REFERENCE TO RELATED APPLICATIONS

This application is a U.S. national stage entry under 35 U.S.C. § 371 of PCT International Patent Application No. PCT/EP2016/073741, filed Oct. 5, 2016, which claims priority to European Patent Application No. 15188354.3, filed Oct. 5, 2015, the contents of which are incorporated herein by reference in their entirety.

FIELD OF THE INVENTION

The present invention is situated in the field of blood sample analyte analysis, more particularly in the field of dried blood sample analysis and in methods for increasing the accuracy of quantitative analyte measurement in such samples by determining the hematocrit of such a sample.

BACKGROUND OF THE INVENTION

Dried blood samples are increasingly being used as an alternative for classical venous blood and plasma. In the analysis of dried blood samples, a major 'unknown', having an impact on the uncertainty of the analytical result, is the hematocrit (Hct), i.e. the volume percentage of red blood cells in blood.

As the Hct cannot be directly measured on dried blood samples, people have tried to estimate this based on the levels of endogenous compounds that correlate with the Hct.

These attempts have for example been reviewed in De Kesel et al., 2013 (Bioanalysis 2013; 5(16):2023-41).

One possible method was to use potassium as a value for red blood cell content, such as reported by Capiau et al., 2013 (Anal Chem. 2013; 85(1):404-10). Although this method showed good results, one drawback is that part of the dried blood sample needs to be sacrificed for the potassium measurement, which is undesirable.

In view of implementation of this method in high-throughput surroundings such as clinical labs or pharmaceutical industry, it is furthermore important that a Hct estimation method is automatable and compatible with existing automated dried blood sample analysers. Furthermore, this method should preferably be non-destructive, as this way no part of the very limited sample volume is consumed and the entire dried blood sample remains available for further analyses.

Another logical candidate Hct marker is hemoglobin, as hemoglobin is also used for this purpose in whole blood samples. However, multiple research groups have tried this and failed. E.g. Miller et al., 2013 (J Anal Bioanal Techniques) report on a method to estimate hematocrit in a dried blood spot comprising measuring hemoglobin via non-contact diffuse reflectance spectroscopy at a wavelength of 980 nm. The reflection obtained at this wavelength is not representative for the hemoglobin in the dried blood sample, but reflects the background scattering of the substrate, which is not specific for hemoglobin. Miller et al further state that although they tried to use the hemoglobin-specific parts of the spectrum (using wavelengths of 540 and/or 570 nm) as a measure for Hct, they did not succeed. Yu and co-workers (Anal. Bioanal. Chem., 2015 Sep. 7) recently reported on another method of quantifying hemoglobin in dried blood spots using a protein spiking method coupled to detection with tandem mass spectrometry; One drawback of this method is that the sample is destroyed and hence cannot be used for further analyte analysis.

Hence, up till now, hemoglobin was considered not suitable for the prediction of the Hct of dried blood samples.

Accordingly, there is a need for improved methods for determining the hematocrit in a dried blood sample, which mitigate at least one of the problems stated above.

SUMMARY OF THE INVENTION

In response to the above indicated problems, the present inventors have developed a non-contact method that allows predicting the Hct of a dried blood sample based on its total hemoglobin content, i.e. the sum of the main hemoglobin derivatives arising due to exposure of the dried blood sample to the air.

Furthermore, the proposed method is non-destructive and hence, excludes manual punching and extraction. This saves time, minimizes the introduction of errors and keeps the dried blood sample intact such that the whole content of the sample remains available for other analyses.

Moreover the risk of carry-over is minimized as this is a non-contact method (no-punching required). The use of non-contact diffuse reflectance spectroscopy also makes this procedure easy to automate and to integrate in automated dried blood sample analysers. Especially in high-throughput environments such as clinical laboratories and pharmaceutical industry, this may be a crucial advantage.

This Hct estimation can be used in a correction algorithm that corrects for the difference in dried blood sample-based results and whole blood-based results. This difference is caused by the hematocrit effect on dried blood sample-analysis. I.e. dried blood samples with low hematocrit values tend to yield an underestimation of the true analyte concentration in whole blood, whilst high hematocrit values tend to lead to overestimation. The extent of this hematocrit effect is compound dependent and can be established using a reference set of dried blood samples and corresponding whole blood samples. Based on this dataset it can be deduced how large the hematocrit effect will be at a certain hematocrit value. If then one can determine the hematocrit of a given dried blood sample, a hematocrit-dependent correction factor can be applied to compensate for the anticipated hematocrit effect.

Also for the conversion of dried blood sample-based results into their corresponding plasma values knowledge of the hematocrit is essential, since the latter influences the distribution of a compound between the blood cells and the plasma compartment, i.e. the blood-to-plasma ratio of a compound.

In addition, the described method could be employed to evaluate whether the hematocrit of a given dried blood sample falls within a predetermined hematocrit range (established during validation) in which the hematocrit effect is still acceptable.

The Hct of dried blood samples is estimated based on their reflectance spectrum measured using non-contact diffuse reflectance spectroscopy. For fresh blood, this spectrum is predominantly composed of oxyhemoglobin (oxy-Hb). As oxyhemoglobin is transformed into different derivatives upon ageing of a dried blood sample, the spectrum also changes with time e.g. due to the transition of oxyhemoglobin into methemoglobin and hemichrome, making an age-independent hemoglobin determination of dried blood samples extremely challenging. Indeed, it is essential to understand this ageing process to allow correct quantitation of hemoglobin and hence, Hct.

The invention therefore provides for the following aspects:

Aspect 1. A preferably non-destructive method of estimating hematocrit in a dried blood sample comprising the following steps:
   a) Measuring the reflectance, absorbance, or transmittance of the total hemoglobin in said dried blood sample measured at one or multiple wavelengths, and
   b) Estimating the Hct in said dried blood sample based on the amount of reflectance, absorbance, or transmittance obtained in step a), wherein said total hemoglobin comprises oxygenated hemoglobin and the derivatives of hemoglobin, especially the oxidative reaction and denaturation derivatives of hemoglobin, hence comprising at least oxyhemoglobin ($HbO_2$, the non-oxidised, oxygenated form of Hb), met-hemoglobin (met-Hb, oxidized with iron being in the $Fe^{3+}$ state) and hemichrome (HC).

Aspect 2. The method according to aspect 1, wherein the reflectance, absorbance, or transmittance of the total hemoglobin is calculated by comparing the respective reflectance, absorbance, or transmittance spectra for each of the components in the dried blood sample with reference spectra of said respective hemoglobin derivatives, using a least square fitting procedure with reference spectra for said different hemoglobin derivatives. More specifically, in the method according to aspect 1, the reflectance, absorbance, or transmittance of the dried blood sample is measured and used to calculate the total hemoglobin content (comprising at least oxyhemoglobin ($HbO_2$, the non-oxidised, oxygenated form of Hb), met-hemoglobin (met-Hb, oxidized with iron being in the $Fe^{3+}$ state) and hemichrome (HC)). This can be done by comparing the respective reflectance, absorbance, or transmittance spectra for each of the components in the dried blood sample or of the combined spectrum of the total Hb components with one or more reference spectra resulting from a known theoretical amount of said different hemoglobin derivatives, e.g. using a least square fitting procedure.

Aspect 3. The method according to aspect 1, wherein the reflectance, absorbance, or transmittance of the total hemoglobin is measured based on the reflectance, absorbance, or transmittance at the quasi-isosbestic point of said hemoglobin derivatives, set between 585 and 595 nm, more preferably between 587 and 591 nm, even more preferably between 588 and 590 nm, and most preferably at about 589 nm.

Aspect 4. The method according to any one of aspects 1 to 3, wherein said method is performed via non-contact diffuse reflectance spectroscopy, preferably using an optical reflectance probe, a multispectral, or hyperspectral camera.

Aspect 5. A non-destructive method of estimating hematocrit (Hct) of whole blood from a dried blood sample prepared from the whole blood, the method comprising:
   a) determining the amount of hemoglobin and its derivatives comprising oxyhemoglobin, met-hemoglobin and hemichrome (total hemoglobin) in a dried blood sample, wherein the amount of the hemoglobin derivatives remains constant in the dried blood spot in function of time, and
   b) estimating the hematocrit from the amount of total hemoglobin, wherein the hematocrit is estimated using a calibration curve providing a correlation between hematocrit and the amount of total hemoglobin in a dried blood sample.

Aspect 6. The method according to aspect 5, wherein the amount of total hemoglobin in a dried blood sample is determined by measuring the reflectance, absorbance, or transmittance of the dried blood sample at the quasi-isosbestic point of hemoglobin and its derivatives.

Aspect 7. The method according to aspect 6, wherein the amount of total hemoglobin in a dried blood sample is determined by calculating the sum of the amounts of each of oxyhemoglobin, met-hemoglobin and hemichrome.

Aspect 8. The method according to aspect 7, wherein the amount of each of oxyhemoglobin, met-hemoglobin and hemichrome is determined by measuring the reflectance, absorbance, or transmittance of the dried blood sample at multiple wavelengths, and comparing the measured spectrum with one or more reference spectra of the respective hemoglobin derivatives.

Aspect 9. The method according to aspect 8, wherein comparing the measured spectrum with reference spectra of said respective hemoglobin derivatives is performed using a least square fitting procedure.

Aspect 10. The method according to aspect 6, wherein the quasi-isosbestic point of said hemoglobin derivatives is set between 585 and 595 nm, preferably between 587 and 591 nm, more preferably between 588 and 590 nm, and most preferably at about 589 nm.

Aspect 11. The method according to any one of aspects 8 to 10, wherein the reflectance, absorbance, or transmittance of the dried blood sample at multiple wavelengths is measured at wavelengths ranging at least from 450 to 750 nm.

Aspect 12. The method according to any one of aspects 1 to 11, wherein additionally the reflectance, absorbance, or transmittance of carboxyhemoglobin and/or sulfhemoglobin is used to estimate the Hct.

Aspect 13. The method according to any one of aspects 1 to 12, wherein said hematocrit estimate allows correction of the difference in dried blood spot-based results and whole blood or plasma-based results.

Aspect 14. The method according to any one of aspects 5 to 13, wherein the calibration curve is established by determining the amount of said hemoglobin derivatives in dried blood samples prepared from calibration samples, such as (whole) blood samples, with a known hematocrit, and plotting the amount of said hemoglobin derivatives against the known hematocrit.

Aspect 15. The method according to any one of aspects 1 to 14, further comprising the use of calibration curves of blood with a mean corpuscular hemoglobin concentration (MCHC) that corresponds to the average of the target population.

Aspect 16. The method according to any one of aspects 1 to 14, wherein said dried blood sample is selected from the group comprising: dried blood spots, dried matrix samples, dried matrix micro-samples, volumetric dried blood samples, and other dried blood samples.

Aspect 17. A system for estimating the Hct in a dried blood sample, comprising:
   a means for measuring the reflectance, absorbance, or transmittance of hemoglobin and its derivatives (total hemoglobin comprising at least oxyhemoglobin ($HbO_2$, the non-oxidised, oxygenated form of Hb), met-hemoglobin (met-Hb, oxidized with iron being in the $Fe^{3+}$ state) and hemichrome (HC)) in a dried blood sample at a wavelength ranging at least from 450 to 750 nm or at a wavelength of 589 nm (+/−5 nm); and
   a computer implemented program for calculating the Hct from such a measurement, using the method according to any one of claims 1 to 16.

Aspect 18. The system according to aspect 17, incorporated into a dried blood sample analyser.

Aspect 19. The system according to aspect 18, wherein said dried blood sample analyser uses on-line elution or desorption technology, automated extraction, automated volumetric absorptive microsampling extraction, or punched disc extraction, or a spectrometric dried blood sample scanning system.

Aspect 20. The system according to any one of aspects 17 to 19, wherein said means for measuring the reflectance, absorbance or transmittance of hemoglobin and its derivatives is a means for performing non-contact diffuse reflectance spectroscopy at a wavelength ranging at least from 450 to 750 nm, or at a wavelength of 589 nm (+/−5 nm).

Aspect 21. The system according to aspect 20, wherein said means for performing non-contact diffuse reflectance spectroscopy comprises a light source, a light guiding means, and a spectral detection means.

Aspect 22. The system according to any one of aspects 17 to 21, wherein said means for performing non-contact diffuse reflectance spectroscopy further comprises a spectral filter between said light guiding means and said spectral detection means.

Aspect 23. The system according to any one of aspects 17 to 22, wherein said means for performing non-contact diffuse reflectance spectroscopy further comprises a computer controlling the light source and collecting the reflectance, absorbance or transmittance data.

Aspect 24. The system according to any one of aspects 17 to 23, wherein said spectral detection means is selected from: a spectrograph; a photodetector; an optical reflectance/backscatter probe system; or a spectral camera such as a staredown camera, a multispectral or hyperspectral imaging camera or a CCD camera.

Aspect 25. The system according to any one of aspects 17 to 24, wherein said light source is capable of emitting light of a wavelength set between at least 450 and 750 nm, preferably wherein said light source is a halogen or LED light source.

Aspect 26. The system according to any one of aspects 17 to 25, wherein said spectral filter is selected from the group of tunable or random access filters.

Aspect 27. A dried blood sample sampler, preferably an autosampler, connected to the system for estimating the Hct from a dried blood sample according to anyone of aspects 17 to 26, wherein said dried blood sample sampler is preferably selected from the group comprising: systems using on-line elution or desorption, automated extraction, automated volumetric absorptive microsampling extraction, punched disc extraction, or spectrometric dried blood sample scanning system.

Aspect 28. A non-destructive method of estimating hematocrit of whole blood from a dried blood sample prepared from the whole blood, the method comprising:
  a) determining the amount of hemoglobin and its derivatives (total hemoglobin) comprising oxyhemoglobin, met-hemoglobin and hemichrome in a dried blood sample by measuring the reflectance, absorbance, or transmittance of the dried blood sample (a1) at the quasi-isosbestic point of said hemoglobin derivatives or (a2) at multiple wavelengths, wherein the amount of said hemoglobin derivatives remains constant in function of time, and
  b1) estimating the hematocrit from the reflectance, absorbance, or transmittance of the dried blood sample measured in (a1), wherein the hematocrit is estimated using a calibration curve established by measuring the reflectance, absorbance, or transmittance at the quasi-isosbestic point of said hemoglobin derivatives of dried blood samples prepared from (at least three) calibration samples, such as whole blood samples, with a known hematocrit; or
  b2) estimating the hematocrit in the dried blood sample from the amount of said hemoglobin derivatives in the dried blood sample determined in (a2), wherein the hematocrit is estimated using a calibration curve established by determining the amount of said hemoglobin derivatives in dried blood samples prepared from (at least three) calibration samples, such as whole blood samples, with a known hematocrit, and wherein the amount of said hemoglobin derivatives is determined by calculating the sum of the amounts of each of oxyhemoglobin, met-hemoglobin and hemichrome, and the amount of each of oxyhemoglobin, met-hemoglobin and hemichrome is determined by measuring the reflectance, absorbance, or transmittance of the dried blood sample at multiple wavelengths, and comparing the measured spectrum with reference spectra of said hemoglobin derivatives.

Aspect 29. A non-destructive method of estimating hematocrit of whole blood from a dried blood sample prepared from the whole blood, the method comprising:
  a) determining the amount of hemoglobin and its derivatives (total hemoglobin) comprising oxyhemoglobin, methemoglobin and hemichrome in a dried blood sample, wherein the amount of said hemoglobin derivatives remains constant in function of time, and
  b) estimating the hematocrit from the amount of said hemoglobin derivatives, wherein the hematocrit is estimated using a calibration curve providing a correlation between hematocrit and the amount of said hemoglobin derivatives in a dried blood sample,
  wherein the amount of said hemoglobin derivatives in a dried blood sample is determined by measuring the reflectance, absorbance, or transmittance of the dried blood sample at the quasi-isosbestic point of said hemoglobin derivatives; or
  wherein the amount of said hemoglobin derivatives in a dried blood sample is determined by calculating the sum of the amounts of each of oxyhemoglobin, met-hemoglobin and hemichrome, wherein the amount of each of oxyhemoglobin, met-hemoglobin and hemichrome is determined by measuring the reflectance, absorbance, or transmittance of the dried blood sample at multiple wavelengths, and comparing the measured spectrum with reference spectra of said respective hemoglobin derivatives.

The method as described herein, i.e. the method according to any one of aspects 1 to 16, and 28 and 29, can be automated by integrating it into an automated dried blood sample analyser. Accordingly, provided herein is a dried blood sample sampler or analyser comprising a means for performing diffuse reflectance spectroscopy at a wavelength ranging from at least 450 to 750 nm and a computer implemented means for calculating the Hct from such a measurement, using the method as defined herein.

In certain embodiments, the calibration curve may be established by determining the amount of said hemoglobin derivatives in dried blood samples prepared from calibration samples, such as (whole) blood samples, with a known hematocrit. In certain embodiments, the calibration curve may be established by determining the amount of said hemoglobin derivatives in dried blood samples prepared from calibration samples, such as (whole) blood samples, with a known hematocrit, and plotting the amount of said hemoglobin derivatives against the known hematocrit.

In certain embodiments, calibration curves may be prepared by providing or preparing at least three calibration samples (e.g., whole blood) with a known hematocrit. In embodiments, dried blood samples may be prepared of the calibration samples. In certain embodiments, the total amount of said hemoglobin derivatives may be determined in the dried blood samples prepared from the calibration samples, for example using the single wavelength or multiple wavelength methods as described herein. In embodiments, the known hematocrit may be plotted on the X-axis and the results of the (total) amount of said hemoglobin derivatives (in arbitrary units) or reflectance, absorbance and transmittance at a quasi-isosbestic point of said hemoglobin derivatives (which correlates with total hemoglobin) may be plotted on the Y-axis, thereby providing a calibration curve. In certain embodiments, the regression model which correlates the (total) amount of said hemoglobin derivatives (in arbitrary units) with the known (or true) hematocrit of the calibration samples may be a power regression model (i.e., $y=ax\textasciicircum-b$).

In certain embodiments, the calibration curve may be a linear model after logarithmic transformation of x and y in the power regression model, i.e., when the log(amount of said hemoglobin derivatives) is plotted against the log (hematocrit).

In certain embodiments, the hematocrit of whole blood prior to drying can be estimated based on a dried blood sample by determining the amount of said hemoglobin derivatives in a dried blood sample, for example using the single wavelength or multiple wavelength methods as described herein, and calculating the estimated hematocrit using the calibration curve (e.g., by solving the equation of the power regression model or linear model to x).

The estimated Hct is slightly dependent on the mean corpuscular hemoglobin concentration (MCHC) of a patient dried blood sample.

The term "mean corpuscular hemoglobin concentration" or "MCHC" generally refers to a measure of the concentration of hemoglobin in a given volume of packed red blood cells. The MCHC is calculated by dividing the hemoglobin by the hematocrit.

Dependent on the MCHC of a person (biological variation), the amount of hemoglobin and its derivatives (total hemoglobin) per hematocrit will be higher or lower. When a person has a higher MCHC, a higher amount of said hemoglobin derivatives is present in the blood per hematocrit. Since the amount of said hemoglobin derivatives is used to estimate the hematocrit of a sample, the MCHC may influence the estimated hematocrit. When a blood sample has a higher MCHC, a higher amount of said hemoglobin derivatives is present, and the estimated hematocrit is higher than samples with a typical MCHC (in adults the MCHC typically ranges from about 32 g/dl to about 36 g/dl). Alternatively, when a blood sample has a lower MCHC, a lower amount of said hemoglobin derivatives is present, and the hematocrit of the samples may be underestimated.

In order to minimize these MCHC dependent errors, calibration curves can be set up in (whole) blood with an MCHC that corresponds to the average of the target population. To exclude variation in MCHC values between calibration curves, and hence the possibility of introducing a bias this way, it may be advisable to utilize reference or artificial calibration materials to set up a calibration curve that generate a similar reflectance as true dried blood sample-based calibrators.

Accordingly, in certain embodiments of the methods or systems as taught herein, the whole blood samples (for preparing the calibration curve) or calibration samples may have a MCHC that corresponds to the average of the target population.

The dried blood sample reflectance spectra can be obtained using an optical reflectance probe or a multi- or hyperspectral camera. To ensure reproducible measurements the dried blood sample can be positioned on a homogenous background and illuminated homogenously, independent of the used optical device. An electrical dark correction can be performed on all reflectance spectra, and all spectra can be normalized against a white reference measurement (e.g. the paper whereon the dried blood sample was spotted). For both the multispectral algorithm approach and the single-wavelength-based approach, a white reference can be used such as a reflectance reference standard e.g. the SpectraIon standard (Labsphere Inc.). Such a set-up can be incorporated in the dried blood sample sampler or analyser according to any one of aspects 26 and 27.

In certain embodiments, the distance between the probe (e.g., optical reflectance probe) or camera (e.g., multi- or hyperspectral camera) and the sample (e.g., dried blood sample or calibration sample) may be from 0.5 cm to 1.5 cm. For instance, the distance between the probe or camera and the sample may be 0.5 cm, 1.0 cm, or 1.5 cm. In certain embodiments, the distance between the probe or camera and the sample may be from 1.0 cm to 1.5 cm. Such a set-up can be incorporated in the dried blood sample sampler or analyser according to any one of aspects 26 and 27.

In certain embodiments, the distance between the probe (e.g., optical reflectance probe) or camera (e.g., multi- or hyperspectral camera) and the sample may be the same or substantially the same for measuring calibration samples and for measuring a dried blood sample. Such a set-up can be incorporated in the dried blood sample sampler or analyser according to any one of aspects 26 and 27.

In certain embodiments, the sample (e.g., dried blood sample or calibration sample) may be positioned substantially perpendicular or slightly tilted to the probe (e.g., optical reflectance probe) or camera (e.g., multi- or hyperspectral camera). In certain embodiments, the angle between the plane of the sample (e.g., dried blood sample card or calibration sample card) and the axis of the probe (e.g., optical reflectance probe) or camera (e.g., multi- or hyperspectral camera) may be approximately 90 degrees, such as between 75 and 105 degrees, preferably between 80 and 100 degrees, more preferably between 85 and 95 degrees. Such a set-up can be incorporated in the dried blood sample sampler or analyser according to any one of aspects 26 and 27.

In certain embodiments such as in a dried blood sample analyser according to any one of aspects 26 or 27, the distance between the probe (e.g., optical reflectance probe) and the sample (e.g., dried blood sample or calibration sample) may be from 0.5 cm to 1.5 cm, and the sample will be positioned substantially perpendicular or slightly tilted to said probe (e.g. the angle between the plane of said sample and the axis of said probe can be about 90 degrees, such as between 75 and 105 degrees, preferably between 80 and 100 degrees, more preferably between 85 and 95 degrees). In certain embodiments, the distance between said probe and said sample may be 0.5 cm, and the angle between the plane of said sample and the axis of said probe can be about 90 degrees. In certain embodiments, the distance between said probe and said sample may be from 1.0 cm to 1.5 cm, and the angle between the plane of said sample and the axis of said probe can be between 80 and 100 degrees. For instance, the distance between said probe and the sample may be 1.0 cm, and the angle between the plane of said sample and the axis of said probe can be about 90 degrees, such as between 75 and 105 degrees, preferably between 80 and 100 degrees, more preferably between 85 and 95 degrees; or the distance between the probe and the sample may be 1.5 cm, and the angle between the plane of said sample and the axis of said probe can be about 90 degrees, such as between 75 and 105 degrees, preferably between 80 and 100 degrees, more preferably between 85 and 95 degrees.

In certain embodiments, the distance between the camera (e.g., multi- or hyperspectral camera) and the sample (e.g., dried blood sample or calibration sample) may be from about 1 cm to 1 m, and the sample will be positioned substantially perpendicular or slightly tilted to said camera (e.g. the angle between the plane of said sample and the axis of said camera can be about 90 degrees, such as between 75 and 105 degrees, preferably between 80 and 100 degrees, more preferably between 85 and 95 degrees). In certain embodiments, the distance between said camera and said sample may be between 10 cm and 1 m, preferably between 20 cm and 1 m, more preferably between 30 cm and 1 m, and the angle between the plane of said sample and the axis of said camera can be about 90 degrees. In certain embodiments, the distance between said camera and said sample may be between 10 cm and 1 m, preferably between 20 cm and 1 m, more preferably between 30 cm and 1 m, and the angle between the plane of said sample and the axis of said camera can be between 80 and 100 degrees. For instance, the distance between said camera and the sample may be between 10 cm and 1 m, preferably between 20 cm and 1 m, more preferably between 30 cm and 1 m, and the angle between the plane of said sample and the axis of said camera can be about 90 degrees, such as between 75 and 105 degrees, preferably between 80 and 100 degrees, more preferably between 85 and 95 degrees.

The recorded spectra can be processed in multiple ways to obtain a good prediction of the dried blood sample Hct. However, they are always based on the underlying knowledge that within an ageing dried blood sample, the hemoglobin is transformed from oxyhemoglobin (Oxy-Hb or $HbO_2$) into methemoglobin (Met-Hb) due to an oxidation-step, and further into hemichrome (HC), a denatured form of hemoglobin. The present inventors demonstrated, for the first time, that the sum of these three compounds (representing "total hemoglobin") remained constant in function of time, yielding a stable hemoglobin measurement and hence leading to a good estimate of the Hct.

A first processing approach of the methods of any one of the aspects above is the use of a least square fitting procedure to fit a light-transport model to the measured dried blood sample spectrum. This light-transport model comprises the absorption coefficients for the different hemoglobin derivatives mentioned above as well as scattering and flattening phenomena. By varying the contributions of the different components of the light-transport model, the algorithm is able to find the combination of parameters yielding a theoretical spectrum resembling the measured spectrum the most. This way the amounts (in arbitrary units) of said different hemoglobin derivatives present in a dried blood sample are estimated. Subsequently the sum of the derivatives (in arbitrary units) is made and can be used to estimate the Hct.

A simplified processing approach of the methods of any one of the aspects above is to only utilize the reflectance at a quasi-isosbestic point (between 585-595 nm, preferably at about 589 nm) of said three main hemoglobin derivatives. The inventors show for the first time that the reflectance at this wavelength is time-independent. Hence, the reflectance at about 589 nm correlates with total hemoglobin in a dried blood sample and hence, Hct. However, the reflectance at this wavelength does not contain any information about the Hb derivative(s) present in the sample.

More specifically, correlating the recorded diffuse reflectance spectrum or spectra to the hematocrit of dried blood samples as in the methods of any one of the above aspects can be done in two general ways: 1) using a multi-wavelength approach or 2) using a single wavelength approach as explained below:

a) Multi-Wavelength Approach:

An existing spectroscopic algorithm, capable of estimating the age of a blood stain based on its relative oxyhemoglobin, methemoglobin and hemichrome content by Bremmer et al. (Forensic Sci Int. 2011), was adapted to allow the absolute quantification of the hemoglobin derivatives, oxyhemoglobin, methemoglobin and hemichrome. The sum of the three absolute quantities of oxyhemoglobin, methemoglobin and hemichrome can be used as a measure of total hemoglobin content and hence, hematocrit. The existing algorithm was adapted by taking out the condition that the amount or sum of the hemoglobin derivatives was equal to a single value. Moreover, a pre-processing step to correct the spectra by applying a standard normal variation (SNV) algorithm was deleted.

In order to obtain quantitative results a flattening factor needed to be integrated in the existing algorithm to account for an experimentally observed hematocrit-dependent spectral flattening. The algorithm looks as follows:

$$R_{dried\ blood\ sample}(\lambda) = \frac{I_{dried\ blood\ sample}(\lambda)}{I_{ref}(\lambda)}$$

wherein:

$I_{dried\ blood\ sample}$ is the intensity of the light reflected by the dried blood sample;

$I_{ref}$ is the intensity of the light reflected by a white reflection standard $R_{dried\ blood\ sample}(\lambda)$ is the reflectance of the dried blood sample material (in a.u.) at wavelength ($\lambda$), Once the reflectance spectra of the dried blood sample ($R_{dried\ blood\ sample}(\lambda)$) and the substrate $R_{sub}(\lambda)$ have been measured, they can be used in a light-transport model in combination with the known absorption coefficients of Oxy-Hb, met-Hb and HC, in order to calculate the amounts of these three Hb derivatives present in a dried blood sample using a least squares fitting procedure. The amounts of Oxy-Hb, met-Hb and HC can then be used to determine the total Hb content, in turn allowing estimation of the Hct.

Also, In order to obtain the quantitative results a different fit range was used for the algorithm namely a fit range of 500-700 nm instead of a fit range of 450-800 nm.

b) Single Wavelength Approach:

Alternatively, the reflectance at 589 nm has been identified as hematocrit dependent and remained stable in function of time. Therefore, the reflectance at this quasi-isosbestic point can also be used as a measure of the hematocrit of the whole blood used to prepare a dried blood sample.

More specifically, a calibration curve can be set up by measuring e.g. 7 dried blood sample calibrators with hematocrit values between 0.20 and 0.65 (0.20 or 20%, 0.27 or 27%, 0.35 or 35%, 0.42 or 42%, 0.50 or 50%, 0.57 or 57%, and 0.65 or 65%) and plotting their $I_{589\ nm}/I_{ref,\ 589\ nm}$ values versus their Hct values. The equation of this calibration curve (which is a power function) can then be used to derive the hematocrit of a dried blood sample with unknown Hct, by measuring its reflectance intensity, I, and the reflectance intensity of a white reference, $I_{ref}$, and introducing those values in the previously obtained calibration equation.

The use of a camera instead of an optical probe has the advantage that extra information can be obtained about the spatial distribution of hemoglobin within a dried blood sample, as a reflectance spectrum is recorded for every pixel of the camera. Also more than one spot can be evaluated at once, and the background information and calibration range is also in the same image as the spots.

In reality there are also other hemoglobin derivatives present in a dried blood sample, such as e.g. carboxyhemoglobin and sulfhemoglobin. Although these are generally only present at relatively low levels, as is demonstrated by the good results of the present method, accounting for the presence of these additional hemoglobin-products, may further improve the Hct estimation. This can be achieved by incorporating the reference spectra of these compounds in the fitting procedure or by including additional wavelengths into the single-wavelength approach that correlate with the levels of these compounds.

The developed method has been laboratory tested and thoroughly validated. Furthermore it has been applied to real patient samples with a wide Hct range (n=288).

The present invention also provides for a correction algorithm, based on the obtained estimated Hct, which is able to compensate for the Hct effect that is observed in dried blood sample analysis.

The above and other characteristics, features and advantages of the concepts described herein will become apparent from the following detailed description, which illustrates, by way of example, the principles of the invention.

BRIEF DESCRIPTION OF THE DRAWINGS

The drawings depicted herein are merely for illustrative purposes and are not to be seen as limiting the invention in any particular way.

DETAILED DESCRIPTION OF THE INVENTION

Figure 1:
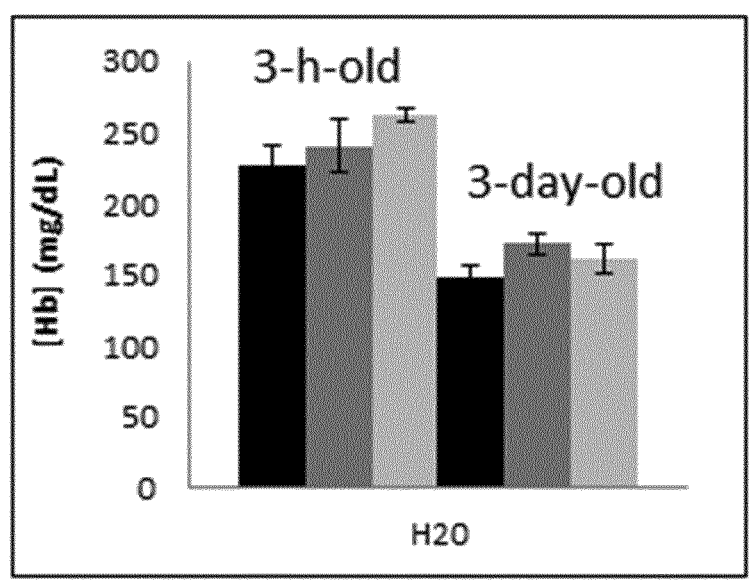
FIG. 1: Instability of hemoglobin in aging dried blood sample measured using a routine chemical analyser (Cobas 8000). It is clear that the apparent amount of hemoglobin has decreased substantially after 3 days already.
Figure 2A:
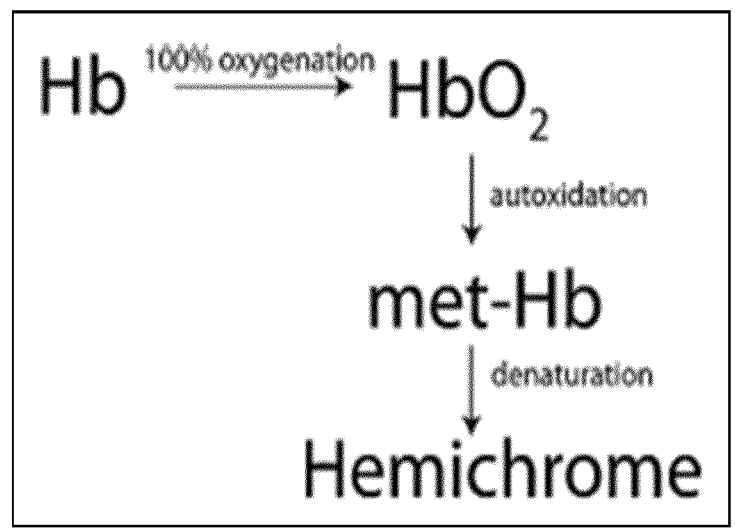
FIG. 2A-2B: Oxidation and degradation forms of hemoglobin. A) Different forms of hemoglobin are formed in blood when contacted with oxygen (air). Substantially all hemoglobin (Hb) will be oxygenated into oxy-hemoglobin ($HbO_2$ or Oxy-Hb) once the blood sample is exposed to the air. Through auto-oxidation, met-hemoglobin (met-Hb) is formed, which is subsequently denatured into hemichrome (HC); B) The absorbance spectra of the different forms of hemoglobin. Three regions of overlap of the three main hemoglobin forms (Oxy-Hb; Met-Hb, and HC) in a dried blood sample can be seen at about 475 nm, between 545-555 nm and between 575-585 nm. (Figures were taken from Bremmer et al. Forensic Sci Int. 2011).
Figure 2B:
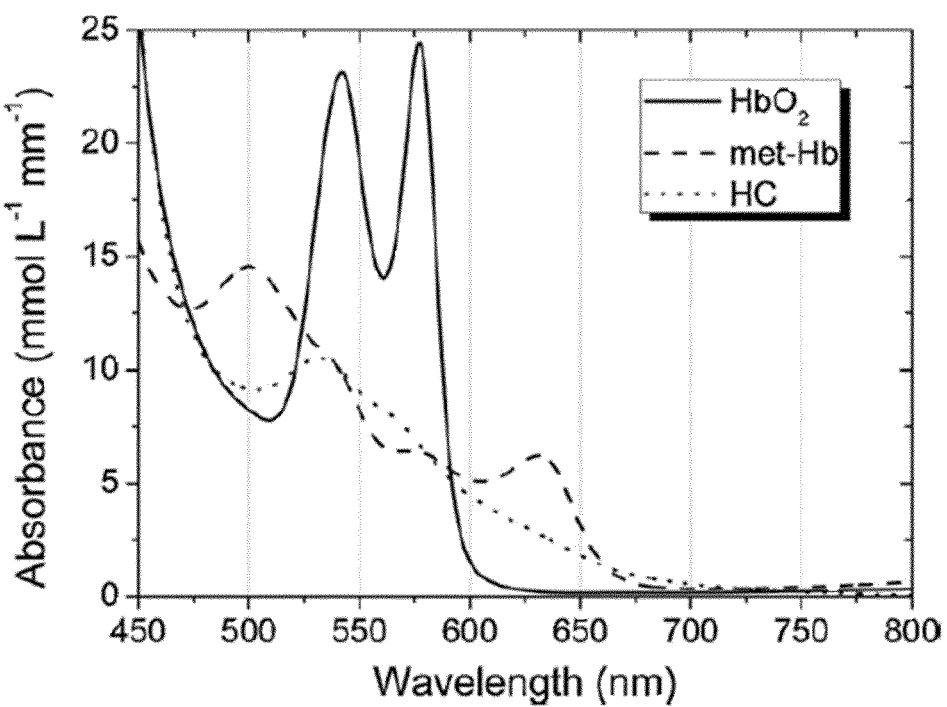
Figure 3:
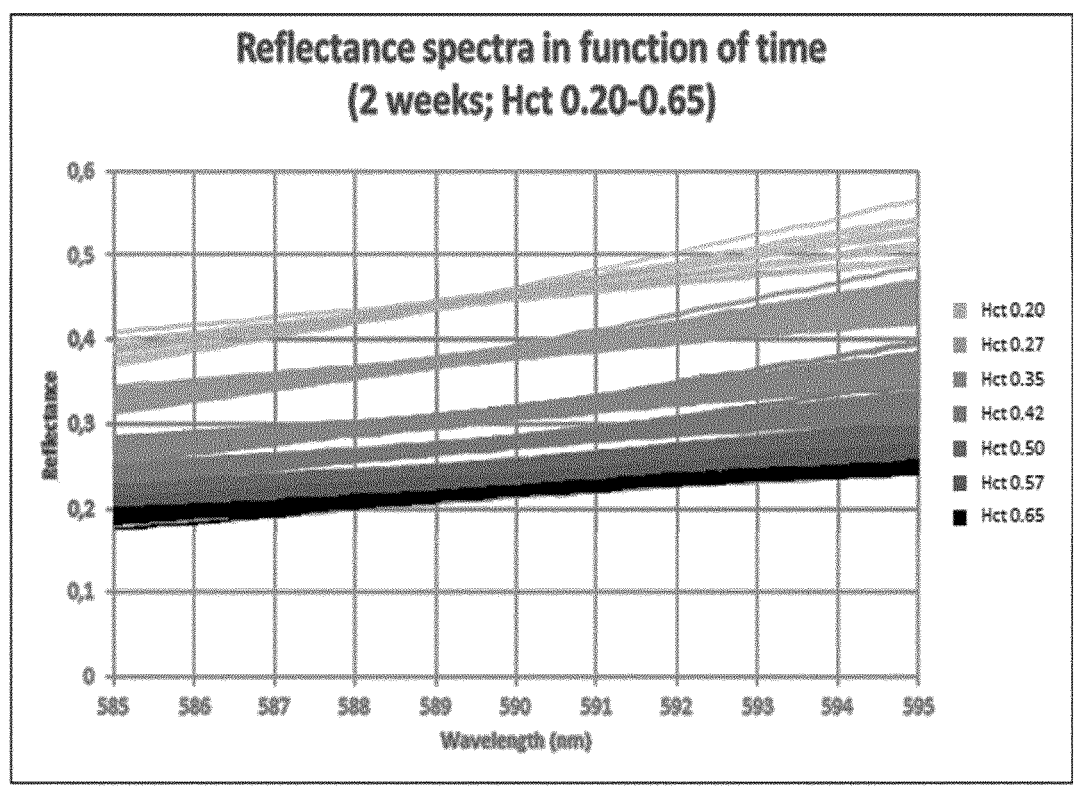
FIG. 3: Reflectance spectra of total hemoglobin (Oxy-Hb, Met-Hb and HC) in function of time. Reflectance spectra of 7 dried blood samples with Hct levels varying between 0.20 and 0.65 were analysed during a period of 2 weeks showing that the reflectance spectrum varies minimally in the region surrounding 589 nm (only the region of 585-595 nm is shown).
Figure 4A:
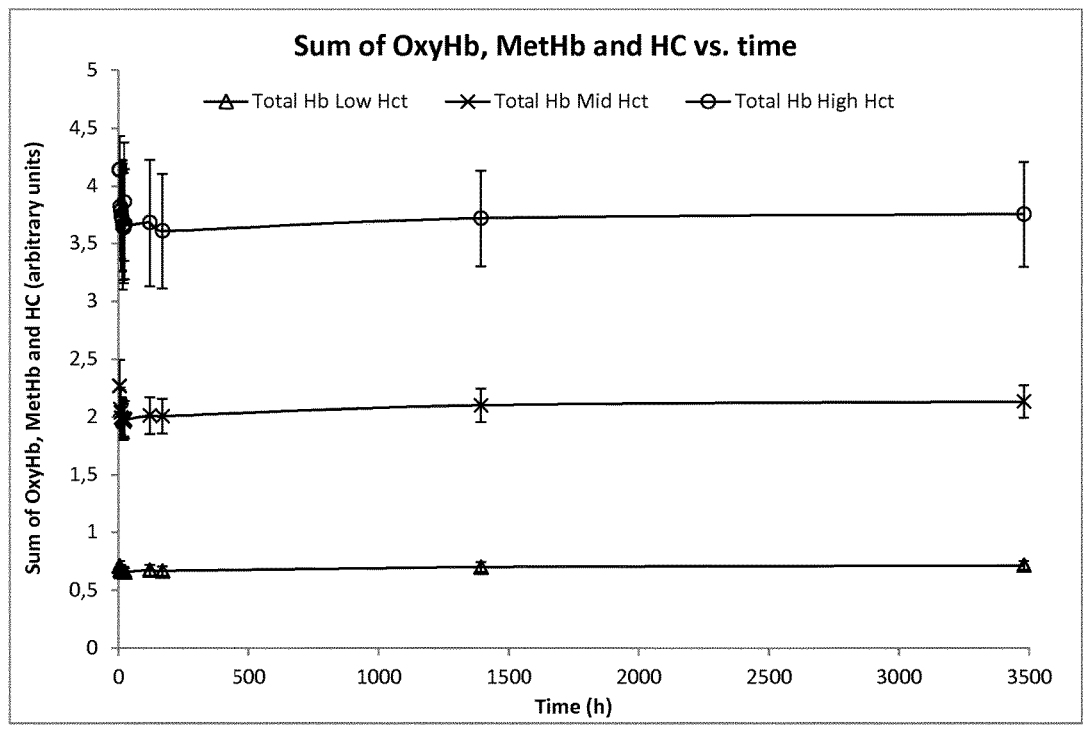
FIG. 4A-4B: Contribution of the three Hb derivatives to total hemoglobin in dried blood samples in function of time and hematocrit. A) Total Hb (in arbitrary units) over time in three samples (each prepared in sixplicate) with different Hct (0.20, 0.42 and 0.65); B) The absolute amount (in arbitrary units) of the three main Hb derivatives (OxyHb, Met-Hb, and HC) over time in three samples (each prepared in sixplicate) with different Hct (0.20, 0.42 and 0.65); Depicted are the average values (n=6) and corresponding standard deviations.
Figure 4B:
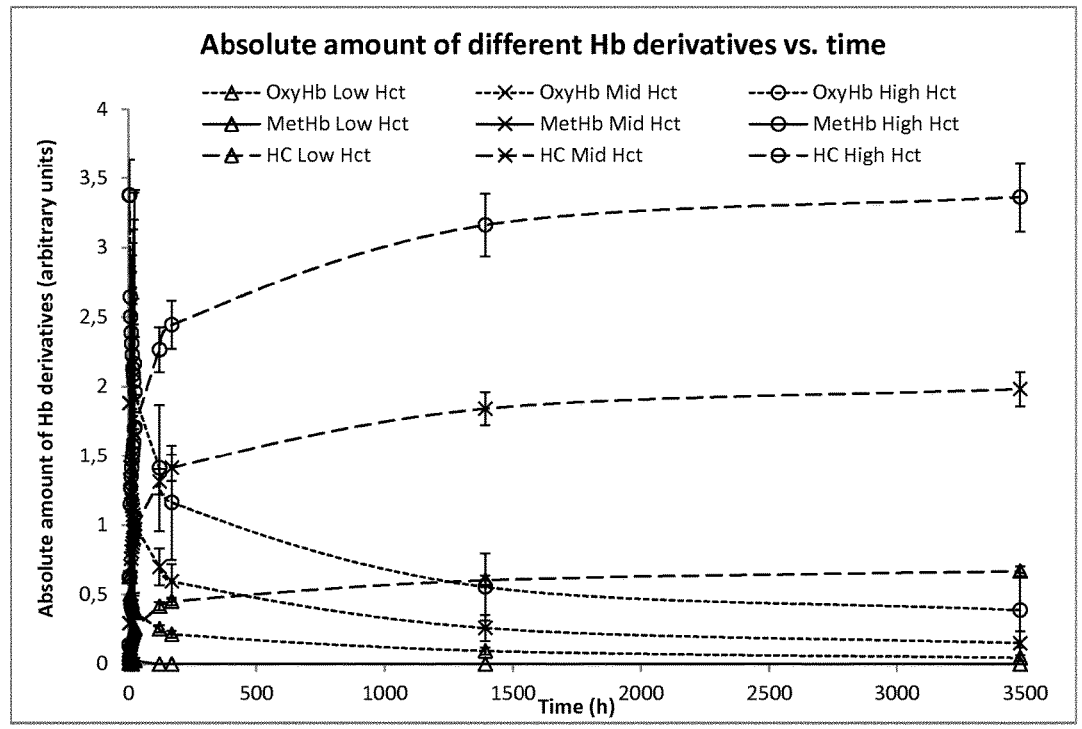

While potentially serving as a guide for understanding, any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited components, elements or method steps also include embodiments which "consist of" said recited components, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments described herein are capable of operation in other sequences than described or illustrated herein.

The values as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to ensure one or more of the technical effects envisaged herein. It is to be understood that each value as used herein is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in disclosing the concepts described herein, including technical and scientific terms, have the meaning as commonly understood by one of ordinary skill in the art. By means of further guidance, definitions for the terms used in the description are included to better appreciate the teaching of the present disclosure.

The terms or definitions used herein are provided solely to aid in the understanding of the teachings provided herein.

Reference throughout this specification to "one embodiment" or "an embodiment" means that a particular feature, structure or characteristic described in connection with the embodiment is included in at least one embodiment envisaged herein. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are also envisaged herein, and form different embodiments, as would be understood by those in the art. For example, in the appended claims, any of the features of the claimed embodiments can be used in any combination.

Through extensive experimental research, the present inventors have realized that the sum of the different hemoglobin derivatives including at least oxyhemoglobin, methemoglobin and hemichrome (total hemoglobin) present in a dried blood sample can be used as a measure of hematocrit independent of the age of the dried blood sample since the sum of the hematocrit derivatives remains constant in a dried blood sample in function of time.

Hence, a first aspect relates to a non-destructive method of estimating hematocrit of whole blood from a dried blood sample prepared from the whole blood, the method comprising: a) determining the (total) amount (in arbitrary units) of hemoglobin and its derivatives comprising oxyhemoglobin, met-hemoglobin and hemichrome in a dried blood sample, wherein the (total) amount (in arbitrary units) of said hemoglobin derivatives remains constant in function of time, and b) estimating the hematocrit from the (total) amount (in arbitrary units) of said hemoglobin derivatives, wherein the hematocrit is estimated using a calibration curve providing a correlation between hematocrit and the (total) amount (in arbitrary units) of hemoglobin derivatives in a dried blood sample.

In certain embodiments of the methods or systems as taught herein, the (total) amount (in arbitrary units) of hemoglobin derivatives in a dried blood sample may be determined by measuring the reflectance, absorbance, or transmittance of the dried blood sample at the quasi-isosbestic point of the hemoglobin derivatives.

In certain embodiments of the methods or systems as taught herein, the (total) amount (in arbitrary units) of hemoglobin derivatives in a dried blood sample may be determined by calculating the sum of the amounts of each of oxyhemoglobin, met-hemoglobin and hemichrome.

In certain embodiments of the methods or systems as taught herein, the amount of each of oxyhemoglobin, met-hemoglobin and hemichrome may be determined by measuring the reflectance, absorbance, or transmittance of the dried blood sample at multiple wavelengths, and comparing the measured spectrum with reference spectra of the respective hemoglobin derivatives.

The term "dried blood sample" indicates all types of blood samples that are left to dry to the air, such as dried blood spots, dried matrix samples, such as dried matrix micro-samples and volumetric dried blood samples, and the like.

The term "hematocrit" as used herein (abbreviated as Hct) is also known as the packed cell volume (PCV) or erythrocyte volume fraction (EVF), and represents the volume percentage (%) of red blood cells in (whole) blood.

The term "estimated hematocrit" as used herein indicates a value calculated using the method according to the present invention, based on the total hemoglobin content of a dried blood sample.

The terms "total hemoglobin", "(total) amount of hemoglobin derivatives" or "(total) hemoglobin content" as used herein indicates the sum (in arbitrary units) of hemoglobin and its derivatives in a dried blood sample formed through exposure to air and mainly comprising hemoglobin, oxygenated hemoglobin (oxyhemoglobin (Oxy-Hb, $HbO_2$), methemoglobin (Met-Hb) and hemichrome (HC), the denatured form thereof. Of note, when hemoglobin exits the body (as is the case with dried blood samples) it is completely oxygenated (and thereby forming oxyhemoglobin) due to its exposure to air and hemoglobin as such will be substantially absent in a dried blood sample. In a next step the oxyhemoglobin can then be oxidized and other hemoglobin forms will be formed. Additional derivatives such as carboxyhemoglobin and/or sulfhemoglobin may also be seen as being incorporated within the terms "total hemoglobin", "(total) amount of hemoglobin derivatives" or "(total) hemoglobin content".

The term "quasi-isosbestic point" as used herein in connection to hemoglobin and its derivatives indicates the wavelength that is overlapping between the three spectra of oxyhemoglobin, methemoglobin and hemichrome. Said wavelength has been determined as lying between 585 and 595 nm, more preferably between 587 and 591 nm, even more preferably between 588 and 590 nm, and most preferably at about 589 nm (+/−5 nm).

The present invention also provides a means for measuring the reflectance, absorbance or transmittance of hemoglobin and its derivatives at a wavelength ranging at least from 450 to 750 nm or at a wavelength of 589 nm (+/−5 nm) (i.e., the quasi-isosbestic point of the hemoglobin derivatives), such as a means capable of performing non-contact diffuse reflectance spectroscopy at a wavelength ranging at least from 450 to 750 nm or at a wavelength of 589 nm (+/−5 nm); and a computer implemented program for calculating the Hct from such a measurement, using the method according to the present invention, which can be integrated or coupled to a dried blood sample (auto)sampler, preferably an automated dried blood sample (auto)sampler.

In a typical set-up, such a system would hence comprise:
a dried blood sample sampler, preferably an autosampler;
a means for measuring the reflectance, absorbance or transmittance of a dried blood sample at a wavelength ranging at least from 450 to 750 nm or at a wavelength of 589 nm (+/−5 nm); and
a computer implemented program for calculating the Hct from such a measurement, using the method according to the present invention.

In a preferred embodiment, said means for measuring the reflectance, absorbance or transmittance of a dried blood sample can be a means performing non-contact diffuse reflectance spectroscopy at a wavelength ranging at least from 450 to 750 nm, or at a wavelength of 589 nm (+/−5 nm).

In certain embodiments, the system as taught herein may be integrated or incorporated in a dried blood sample analyser.

The term "dried blood sample sampler" or "dried blood sample analyser" as used herein represents any type of device that is able to analyse dried blood samples (not necessarily limited, preferably in an automated manner). Such analysers can either use on-line elution or flow-through desorption technology, wherein the analytes are washed out of the carrier material (e.g. the paper or card comprising the dried blood spot, or the matrix comprising the dried blood sample) bringing the dried blood sample sample directly into the analytical system of the analyser; or they can have other ways of automated extraction of dried blood; or they can use punched discs from the dried blood sample paper or card. A non-limiting example of such an analyser is the one described in U.S. Pat. No. 8,586,382 B2 commercialised by Spark Holland. Further examples are volumetric absorptive microsampling (VAMS) analysers. In addition, the hematocrit estimation could also be incorporated in a spectrometric dried blood sample scanning system such as a card-scan device, comprising a light source capable of shining light through a dried blood spot card and a detector quantitating the light absorbed by the bloodspot. One non-limiting commercial example is the Luminex Cardscan™, which uses spectroscopy to evaluate the quality of a dried blood sample.

The means for measuring the reflectance, absorbance or transmittance of a dried blood sample at a wavelength ranging at least from 450 to 750 nm or at a wavelength of 589 nm (+/−5 nm) as used herein refers to any type of means that can measure the amount of light absorbed by hemoglobin and its derivatives (or together referred to herein as "hemoglobin derivatives"). This can either be done by measuring the amount of light reflected by said hemoglobin and derivatives, which is inversely correlated to the amount of light absorbed by said hemoglobin or derivatives. Alternatively, the amount of light retained by the hemoglobin or its derivatives in the blood sample can be measured through analyzing the amount of light transmitted through the blood spot, taking into account reference absorbance parameters of e.g. the blood spot card material and the thickness of the dried blood sample. Said means is hence not limited to a specific measurement method, technology or system, provided said system can detect the amount of light reflected, or absorbed by or transmitted through said dried blood sample without needing to contact the sample. A preferred example of such technology is non-contact diffuse reflectance spectroscopy.

The term "non-contact diffuse reflectance spectroscopy" as used herein is indicative for any type of spectroscopy technique that can detect the reflectance of a dried blood sample as defined herein in a non-invasive manner, i.e. without contacting the dried blood sample itself. Non-limiting examples are optical reflectance/backscatter probes, carrying a light source and light reflection capturing means, connected to a camera such as a camera (e.g. a multispectral or hyperspectral imaging camera or a CCD camera) or a through a light guiding means (e.g. through fibre-optics), typically equipped with a spectral filter (tunable or random access wavelength filter) between the camera and the light guiding means. This allows the registration of the complete spectrum (tunable filter), or of a specific wavelength (random access). Said light source, filter, and camera can be connected to, and operated by, a computer collecting the spectral data. Alternatively a staredown camera system or a pushbroom or whiskbroom camera set-up can be used. The light source can be any suitable light source capable of emitting light of between 450 and 750 nm, such as a halogen light source, or an LED light source. The spectral filters should allow determination of (selected parts of) the reflectance spectra of the three main Hb derivatives, oxyhemoglobin, met-hemoglobin and hemichrome, and is typically set between 450 and 750 nm. One non-limiting example can be an Acoustic Optical Tunable Filter (AOTF) such as the one from Gooch and Housego (UK) or the Liquid Crystal Tuneable Filter (LCTF), the VariSpec from Cri (US).

The computer controlling the light source and collecting the reflectance data can further comprise a computer program able to estimate the Hct of the dried blood sample using the method as disclosed herein, wherein the total hemoglobin is measured as the sum of hemoglobin, oxyhemoglobin (the oxygenated form of Hb) and all oxidative reaction or denaturation products of oxyhemoglobin, i.e. comprising at least: oxyhemoglobin, methemoglobin and hemichrome, the method encompassing determining the amount of each of oxyhemoglobin, met-hemoglobin and hemichrome by measuring the reflectance, absorbance, or transmittance of the dried blood sample at multiple wavelengths, and comparing the measured spectrum with reference spectra of the respective hemoglobin derivatives. Said comparing of the measured spectrum with reference spectra of said respective hemoglobin derivatives is preferably done using a least square fitting procedure. In essence, the reflectance ratio of the sample and its background $R(\lambda)=I(\lambda)/I_{ref}(\lambda)$ were analyzed with a multi-component linear least squares fit. The absorption spectra of the three compounds present in blood: oxy-hemoglobin, met-hemoglobin and hemichrome were used as input. A light transport model was employed to translate the absorption spectra into a reflectance spectrum. The fitting algorithm varies the amplitudes of the three absorption spectra, in order to find the combination of the three with a minimum of difference between the theory and the diffuse reflectance spectrum.

Aside from the amplitude of the three Hb-spectra, also the thickness of the substrate, the scattering power, the scattering height and the flattening can be varied until the measured spectrum fits best with the theoretic spectrum constructed by the specific values for all these parameters. The thickness for the substrate can be kept constant for the performed data-analysis, if the same type of filter paper substrate is used throughout the measurements. The correlation of the value for total Hb obtained after application of the algorithm with the true Hct of the sample was best described using a linear regression model after logarithmic transformation.

Alternatively, the computer controlling the light source and collecting the reflectance data can further comprise a computer program able to estimate the Hct of the dried blood sample using the method as disclosed herein, wherein the total hemoglobin in said dried blood sample is measured based on the reflectance at the quasi-isosbestic point representative for said hemoglobin variants, which was determined herein as being 589 nm (+/−5 nm), using a power function regression model. The regression model which correlates the measured reflectance with the true Hct of the samples was a power regression model. In essence, the equation looked like $y=a*x^{-b}$ with $y=I_{589\ nm}/I_{ref,\ 589\ nm}$ and x=Hct. The value of 'a' and 'b' depends on the specific results for each calibration curve.

EXAMPLES

The following examples are provided for the purpose of illustrating the claimed methods and applications and by no means are meant and in no way should be interpreted to limit the scope of the present invention.

Example 1. Development, Validation and Application of a Non-Destructive Hematocrit Estimation Method for Dried Blood Spots (DBS) Using Non-Contact Diffuse Reflectance Spectroscopy First it was evaluated whether it would be possible to quantitatively measure different hemoglobin derivatives (i.e. oxyhemoglobin (Oxy-Hb), methemoglobin (Met-Hb) and hemichrome (HC), present in a dried blood sample, in particular a dried blood spot (DBS) and whether the sum of these compounds could be used as a measure of hematocrit, independent of the age of the dried blood sample. Moreover, other ways to deduce the hematocrit of a dried blood sample from its reflectance spectrum were evaluated.

I. Method Development and Optimization:

Correlating the recorded diffuse reflectance spectrum to the hematocrit of dried blood samples a) Multi-Wavelength Approach:

An existing spectroscopic algorithm as described by Bremmer et al. Forensic Sci Int. 2011 was developed to allow age estimation of blood stains at crime scenes and was based on the fractions of oxyhemoglobin, methemoglobin and hemichrome in a blood stain. In the existing algorithm, the amount of hemoglobin derivatives (i.e., oxyhemoglobin, methemoglobin and hemichrome) was kept equal to one single value (e.g. close to 1) since only the proportion of the hemoglobin derivatives was important. So, independently from the hematocrit (and hence independently from the amount of the hemoglobin derivatives), the amount of hemoglobin derivatives was equal to one single value. Hence, the existing algorithm could not be used to estimate hematocrit.

The present inventors have realized that the amount of total hemoglobin, i.e. the amount of oxygenated hemoglobin ($HbO_2$) and its oxidized derivatives such as methemoglobin and hemichrome in a dried blood sample could be used to estimate hematocrit of whole blood (from which the dried blood sample is prepared) independently of the age of the dried blood spot.

The existing spectroscopic algorithm by Bremmer et al., although capable of estimating the age of a blood stain based on its relative oxyhemoglobin, methemoglobin and hemichrome content, needed to be adapted to allow the absolute quantification of these three hemoglobin derivatives and hence the estimation of the hematocrit in a sample regardless of the age thereof by calculating the sum of these three absolute quantities (oxyhemoglobin, methemoglobin and hemichrome) as a measure of total hemoglobin content and hence, hematocrit. The existing algorithm was adapted by taking out the condition that the amount or sum of the hemoglobin derivatives was equal to a single value. Moreover, a pre-processing step to correct the spectra by applying a standard normal variation (SNV) algorithm was deleted.

In order to obtain quantitative results a flattening factor needed to be integrated in the existing algorithm to account for an experimentally observed hematocrit-dependent spectral flattening. The changes to the algorithm were made by the Department of Biomedical Engineering and Physics, who also developed the original algorithm as described by Van Veen et al., 2002, Optics letters, Vol. 27(4), pp. 246-8 and as described in WO2009130580A1.

$$R_{dried\ blood\ sample}(\lambda) = \frac{I_{dried\ blood\ sample}(\lambda)}{I_{ref}(\lambda)}$$

wherein:

$I_{dried\ blood\ sample}$ is the intensity of the light reflected by the dried blood sample;

$I_{ref}$ is the intensity of the light reflected by a white reflection standard $R_{dried\ blood\ sample}(\lambda)$ is the reflectance of the dried blood sample material (in a.u.) at wavelength ($\lambda$), Once the reflectance spectra of the dried blood sample ($R_{dried\ blood\ sample}(\lambda)$) and the substrate $R_{sub}(\lambda)$ have been measured, they can be used in a light-transport model in combination with the known absorption coefficients of Oxy-Hb, met-Hb and HC, in order to calculate the amounts of these three Hb derivatives present in a dried blood sample using a least squares fitting procedure. The present amounts of Oxy-Hb, met-Hb and HC can then be used to determine the total Hb content, in turn allowing estimation of the Hct.

Also, In order to obtain the quantitative results a different fit range was used for the algorithm namely a fit range of 500-700 nm instead of a fit range of 450-800 nm.

b) Single Wavelength Approach:

Dried blood samples, in particular DBS, with different hematocrits were measured repeatedly over the course of two weeks. When comparing the recorded spectra, it was observed that the reflectance at 589 nm was hematocrit dependent and remained stable in function of time. Therefore, the reflectance at this quasi-isosbestic point was also used as a measure of the hematocrit of the whole blood used to prepare a dried blood sample. More specifically, a calibration curve can be set up by measuring 7 dried blood sample calibrators with hematocrit values between 0.20 and 0.65 (0.20 or 20%, 0.27 or 27%, 0.35 or 35%, 0.42 or 42%, 0.50 or 50%, 0.57 or 57%, and 0.65 or 65%) and plotting their $I_{589\ nm}/I_{ref,\ 589\ nm}$ values versus their Hct values. The equation of this calibration curve (which is a power function, as was described above) can then be used to derive the hematocrit of a dried blood sample with unknown Hct, by measuring its reflectance intensity, I, and the reflectance intensity of a white reference, $I_{ref}$, and introducing those values in the previously obtained calibration equation.

II. Method Validation

For all method validation experiments, dried blood samples were first measured using the optical probe and subsequently measured using the camera set-up.

Independent of how the reflectance spectra were recorded, they can be analysed using either the multi-wavelength or the single wavelength approach described above. Although data analysis has not yet been completed for all the different approaches described, they yield similar results.

Data-analysis of the spectra obtained using the optical probe led to the following results:

a) Setting Up the Calibration Model:

When only taking the reflectance at 589 nm into account a power function regression model outperformed other calibration models.

The regression model which correlates the measured reflectance with the true Hct of the samples was a power regression model: $y=a*x-b$., with $y=I_{589\ nm}/I_{ref,\ 589\ nm}$ and $x=Hct$. The value of 'a' and 'b' depends on the specific results for each calibration curve.

For the multi-wavelength approach the correlation between the estimated total hemoglobin content and the hematocrit was described by a linear model after logarithmic transformation. On the x-axis the log(true hematocrit) is plotted and on the y-axis the log(total hemoglobin in arbitrary units).

b) Evaluating Homoscedasticity

After performing a Levene's test, data proved to be homoscedastic.

c) Evaluating Accuracy and Precision

Both for the single wavelength and the multi-wavelength approach the developed method proved to be sufficiently accurate and precise (i.e. <15% deviation). To assess this, two calibration curves were set up on each of three different days. Along with every calibration line, three dried blood sample QCs with a low, normal and high Hct were prepared from blood of the same donor. For lower limit of quantitation (LLOQ), upper limit of quantitation (ULOQ) and all three QC levels % bias and % RSD never exceeded the 15% limit. This experiment was also carried out using the blood of a second donor, yielding similar results. Even when the QCs of donor 1 were inserted in the calibration equation of donor 2 (or vice versa) the results always complied with the acceptance criteria. Moreover, QCs prepared from four additional blood sources were fitted into the calibration curves of donor 1 and donor 2, leading to excellent results.

TABLE 1

Overview of accuracy and precision data (n = 6). A & B) Data for QCs, LLOQ and ULOQ prepared from blood from the same donor as the calibration curve. C) Data for QCs prepared from blood from the other donors.

|  | Accuracy (% bias) | Intraday precision (% RSD) | Interday precision (% RSD) |
|---|---|---|---|
| QC LOW | −1.46% | 4.44% | 4.61% |
| QC MID | −0.59% | 5.96% | 6.55% |
| QC HIGH | −0.37% | 5.52% | 5.52% |
| LLOQ | 0.15% | 1.97% | 3.15% |
| ULOQ | 0.15% | 2.49% | 2.95% |
| QC LOW (donor 2) | 1.09% | 4.37% | 8.00% |
| QC MID (donor 2) | −4.69% | 4.01% | 4.82% |
| QC HIGH (donor 2) | −3.18% | 5.06% | 5.06% |
| QC LOW (donor 3) | 4.89% | 3.44% | 3.44% |
| QC MID (donor 3) | 4.23% | 1.33% | 1.66% |
| QC HIGH (donor 3) | 1.60% | 3.98% | 4.32% |
| QC LOW (donor 4) | 3.06% | 5.60% | 5.60% |
| QC MID (donor 4) | −0.07% | 9.13% | 9.13% |
| QC HIGH (donor 4) | −4.00% | 6.74% | 7.03% |
| QC LOW (donor 5) | 5.16% | 6.08% | 6.08% |
| QC MID (donor 5) | −2.38% | 5.24% | 5.24% |
| QC HIGH (donor 5) | −0.27% | 9.03% | 9.03% |
| QC LOW (donor 6) | 6.16% | 8.62% | 8.62% |
| QC MID (donor 6) | 3.89% | 9.90% | 9.90% |
| QC HIGH (donor 6) | 2.05% | 7.56% | 7.88% | d) Influence of Dried Blood Sample Storage Conditions on Estimated Hct

Figure 5A:
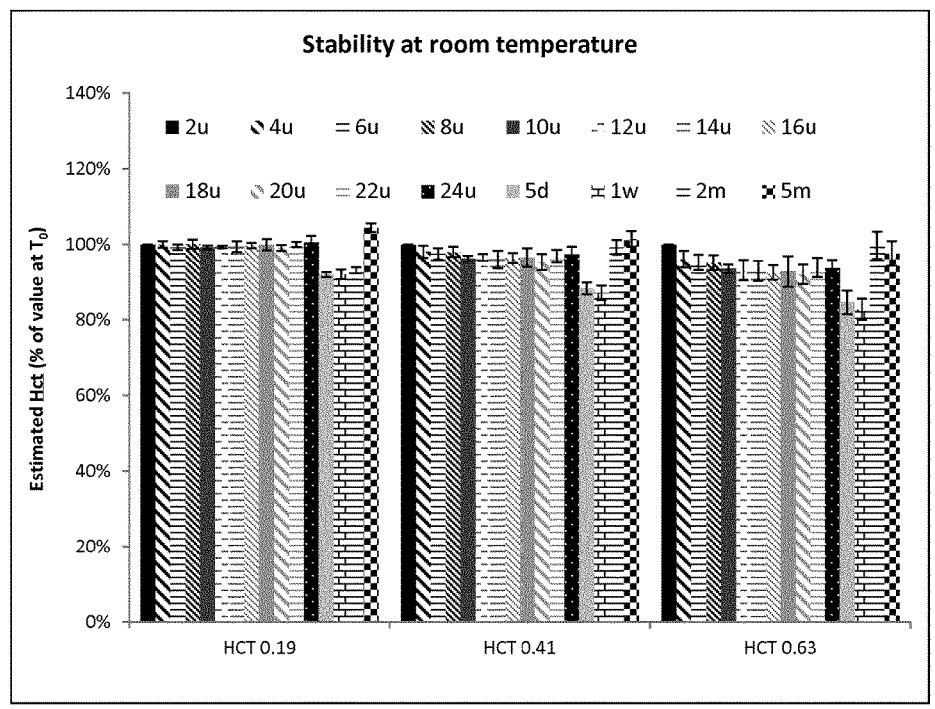
FIG. 5A-5B: Stability of the estimated Hct value over time, when measured with the method according to the invention. A) Influence of storage at room temperature (RT) up to 5 months on the estimated Hct. Values were normalized against values at the start of the experiment ($T_0$); B) Influence of storage at elevated temperatures. Values were normalized against control (=dried blood sample stored at RT).
Figure 5B:
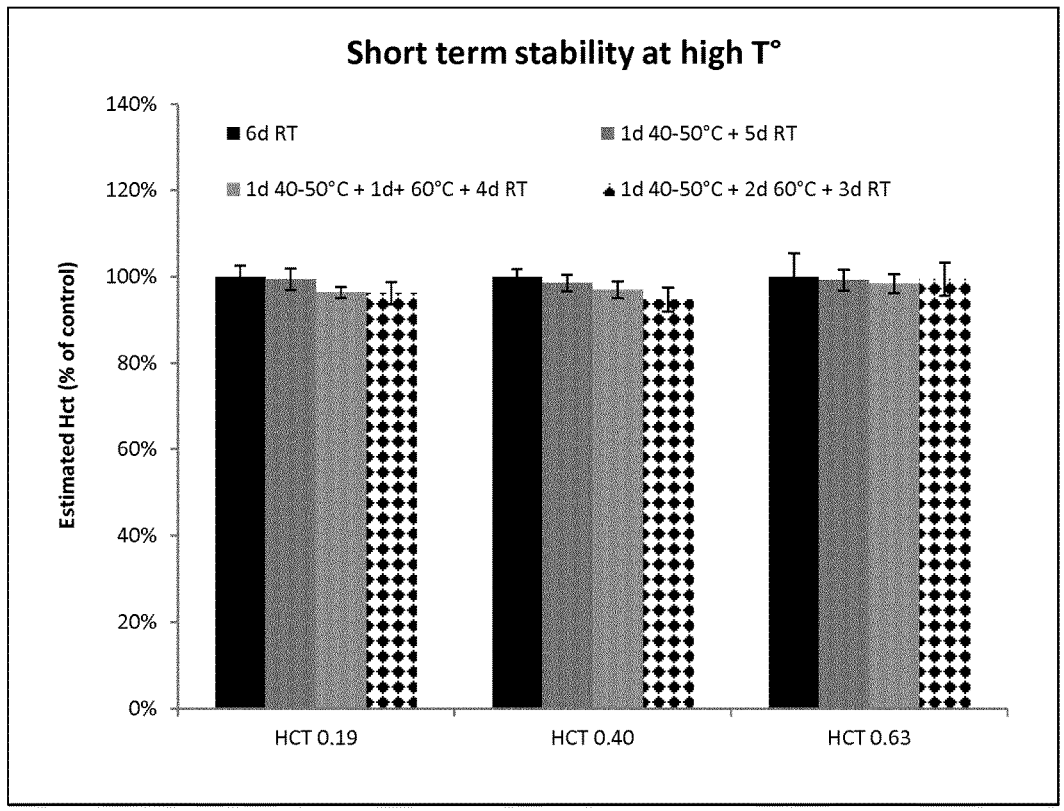

Both for the single wavelength as the multi wavelength approach the influence of storage time on the estimated hematocrit proved to be limited. Long term stability at room temperature did not seem to pose a problem for at least five months, as for the low, normal and high hematocrit levels tested, the observed differences never exceeded ±15% on average at all measured time points. Also short term storage at elevated temperatures (60° C. up to three days) did not lead to relevant differences with dried blood sample stored at room temperature for the same amount of time (see FIG. 5 panel A and B).

e) Evaluation of the Influence of Dried Blood Sample Volume (Volume Effect)

Figure 6A:
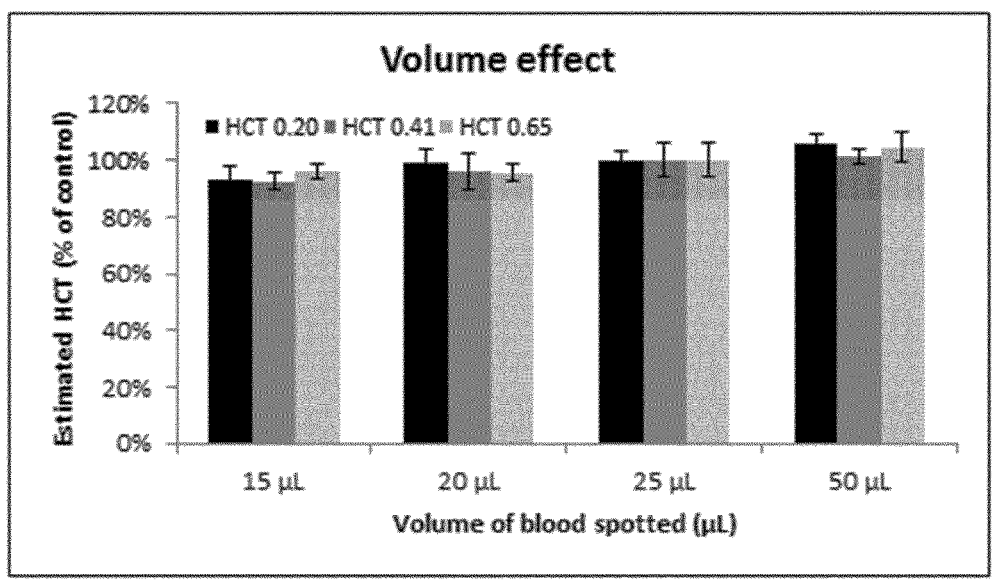
FIG. 6A-6B: Effect of sample volume and measurement location on estimated Hct values. A) Effect of different volumes of blood spotted on estimated Hct. Values were normalized against results at 25 µL; B) Effect of measurement location on the estimated Hct. All parameters were evaluated at three Hct levels. In each panel mean±standard deviation is depicted (n=6).
Figure 6B:
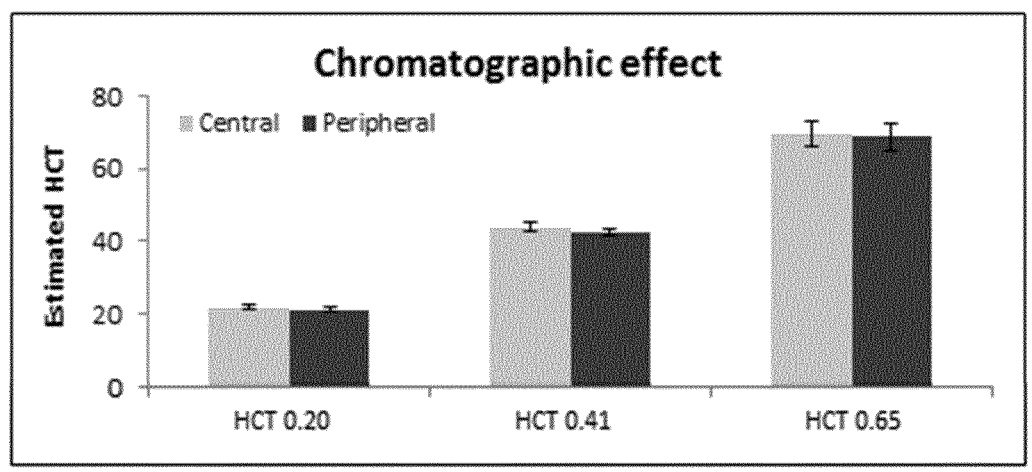

The impact of the blood volume spotted proved negligible when comparing 15, 20, 25 or 50 μL dried blood sample. This experiment was conducted for low, normal and high hematocrit (see FIG. 6 panel A).

f) Evaluation of the Influence of Measurement Location (Volcano Effect)

Hematocrit estimation based on measurements at the center of the dried blood sample and at a more peripheral location, yielded comparable results. This experiment was conducted for low, normal and high hematocrit (see FIG. 6 panel B).

III. Method Application

Figure 7A:
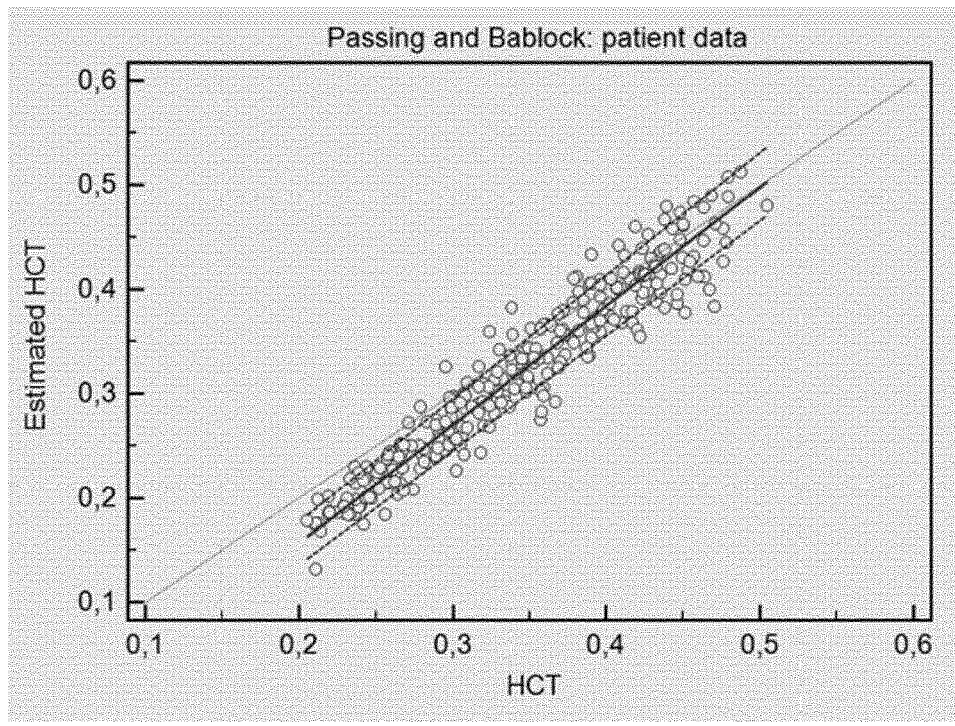
FIG. 7A-7B: Evaluating performance of the method. A) Passing and Bablok regression analysis of estimated Hct value vs. true Hct of patient samples (n=288) (slope [1.1035-1.1813] and intercept [−0.08543; −0.05886]); B) Bland and Altman plot comparing estimated and true Hct of the patient samples (n=288).
Figure 7B:
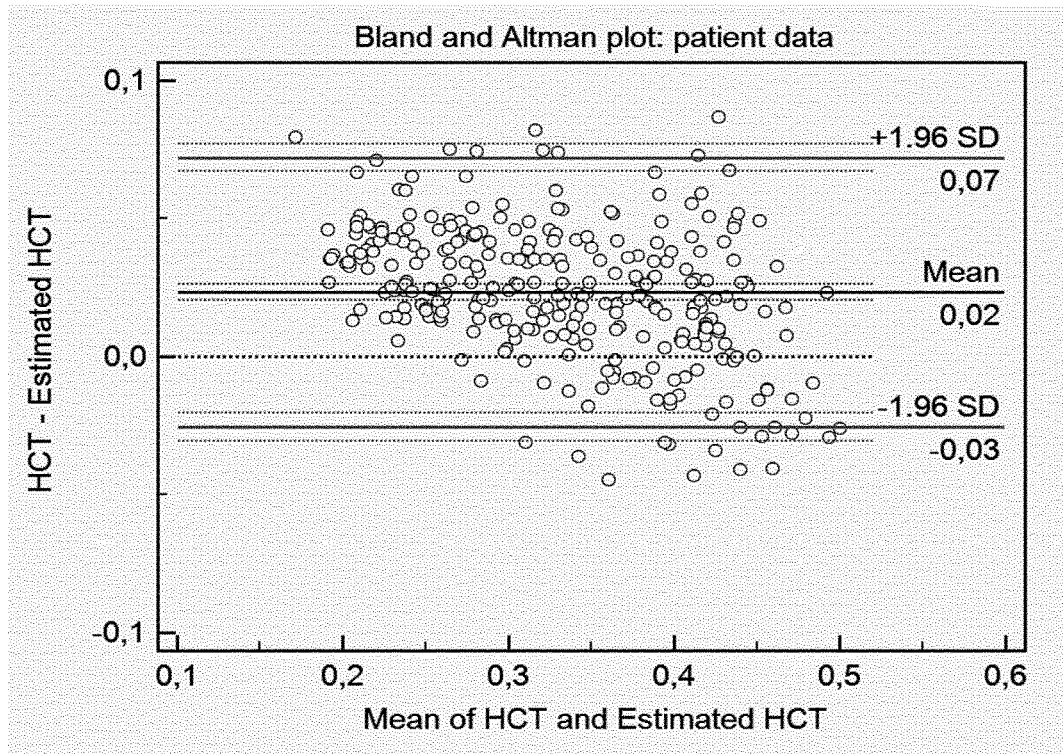
Figure 8:
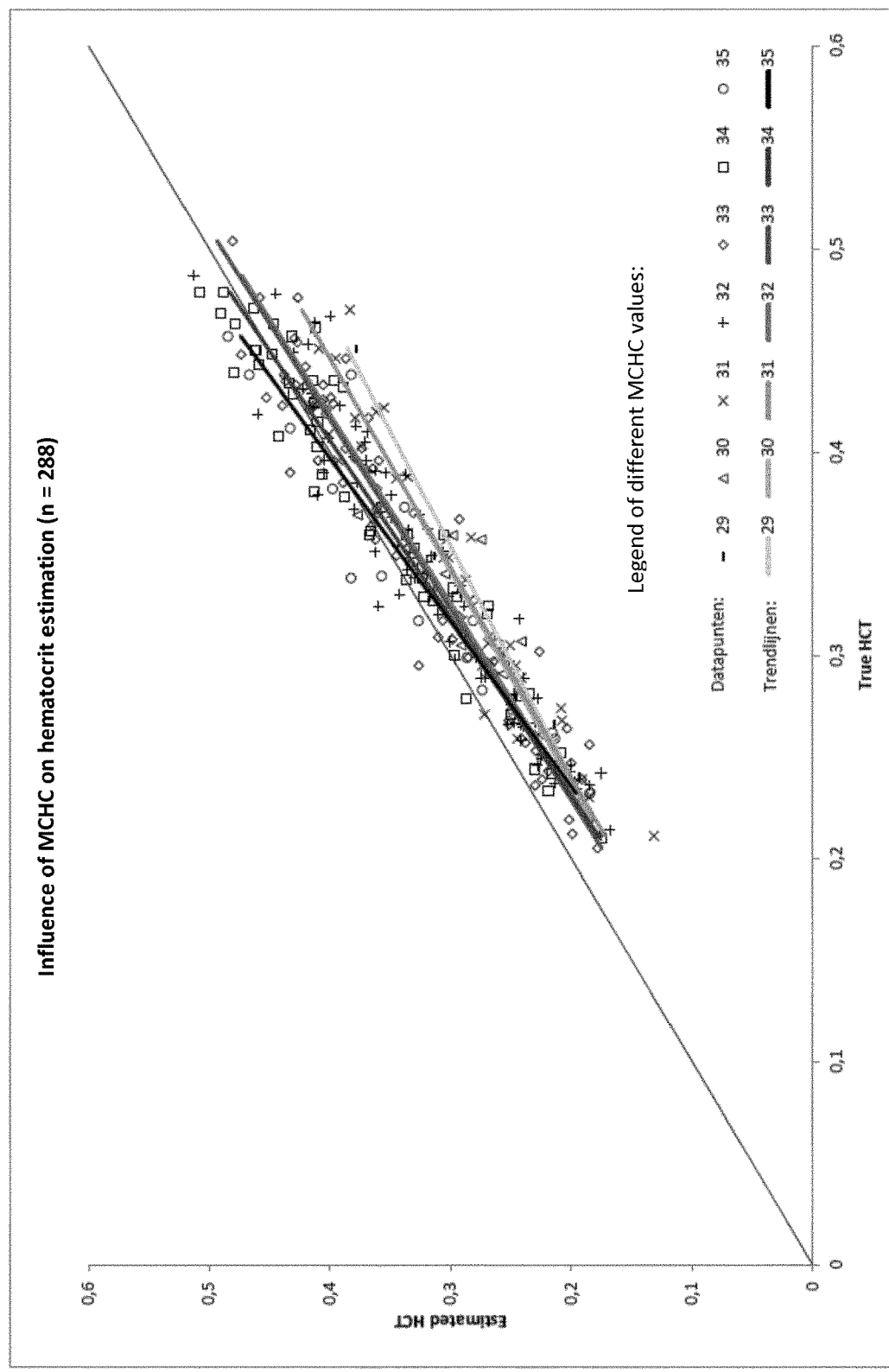
FIG. 8: Influence of the MCHC value of patient samples on the correlation between true Hct and estimated Hct.

Application to Patient Samples with Known Hematocrit:

The developed method was applied on real-life patient samples displaying a wide hematocrit range (0.205-0.504). Ethylenediaminetetraacetic acid anticoagulated left-over samples (n=288) were collected and from each of these dried blood sample were prepared. The hematocrit, estimated using the method according to the present invention, was compared to the true Hct of the samples measured using a Sysmex XE 5000 hematology analyser on corresponding whole blood samples, using Passing and Bablok (See FIG. 7A) regression analysis and a Bland and Altman plot (See FIG. 7B). Although both methods showed good agreement, they were significantly different as the 95% confidence intervals (CI) of slope [1.1035-1.1813] and intercept [−0.08543; −0.05886] did not contain 1 and 0, respectively. Despite this statistically significant difference, our method proved to be fit for purpose, as 234 out of 288 samples (or 81%) were within ±15% of their true Hct value, whilst 270 out of 288 samples (or 94%) were within ±20%.

a) Incurred Sample Reanalysis

Figure 9:
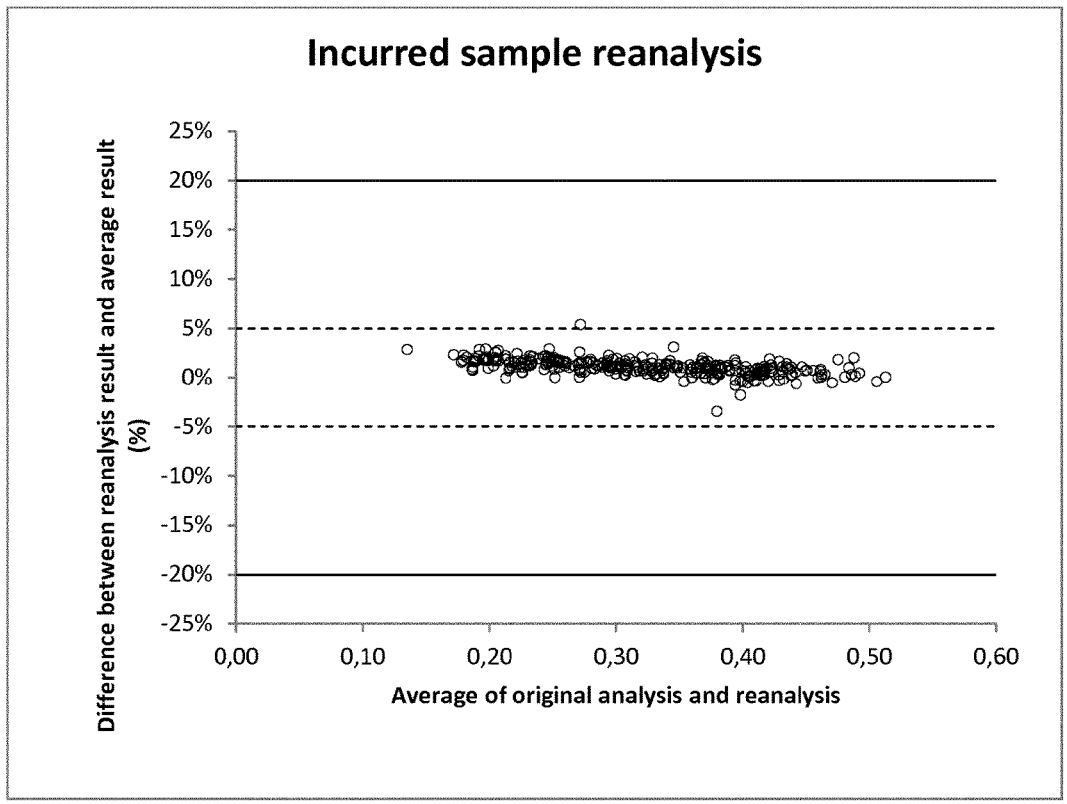
FIG. 9: Reanalysis results of same dried blood samples after 3 days. Comparison of estimated Hct value, measured at $T_0$ and at three days, in the same dried blood sample. For each of the analyses fresh calibration curves were prepared.
Figure 10A:
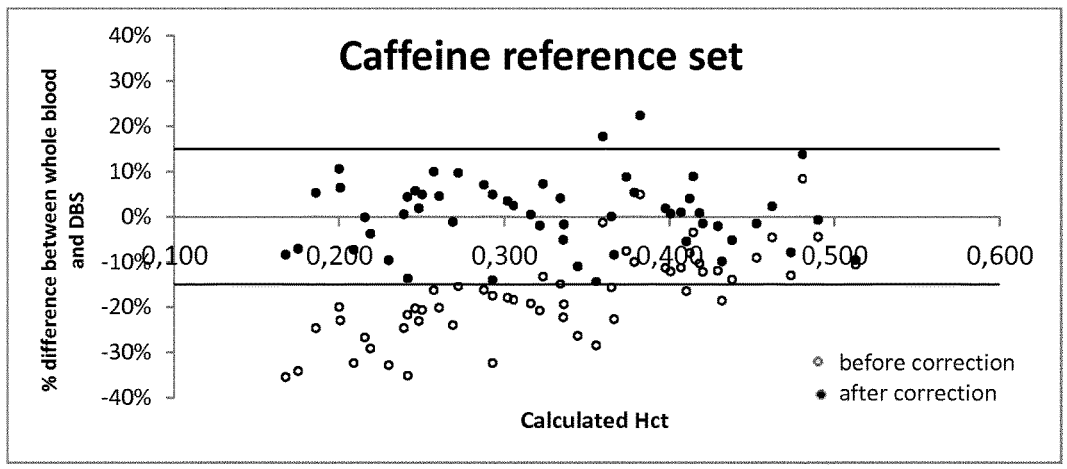
FIG. 10A-10C: The set-up and application of a Hb-based correction algorithm to compensate for the difference between dried blood sample-based results and whole blood-based results. A) The set-up of the correction algorithm on a reference set of caffeine containing samples. To that end, caffeine was measured in both dried blood samples and corresponding whole blood samples and the ratio of the dried blood sample-based result and the whole blood-based results plotted versus the true hematocrit value of the whole blood samples measured using a Sysmex XE 5000 hematology analyser. B) The application of the correction algorithm on an independent test-set of caffeine containing samples. C) The application of the correction algorithm on a set of paraxanthine (a metabolite of caffeine) containing samples.
Figure 10B:
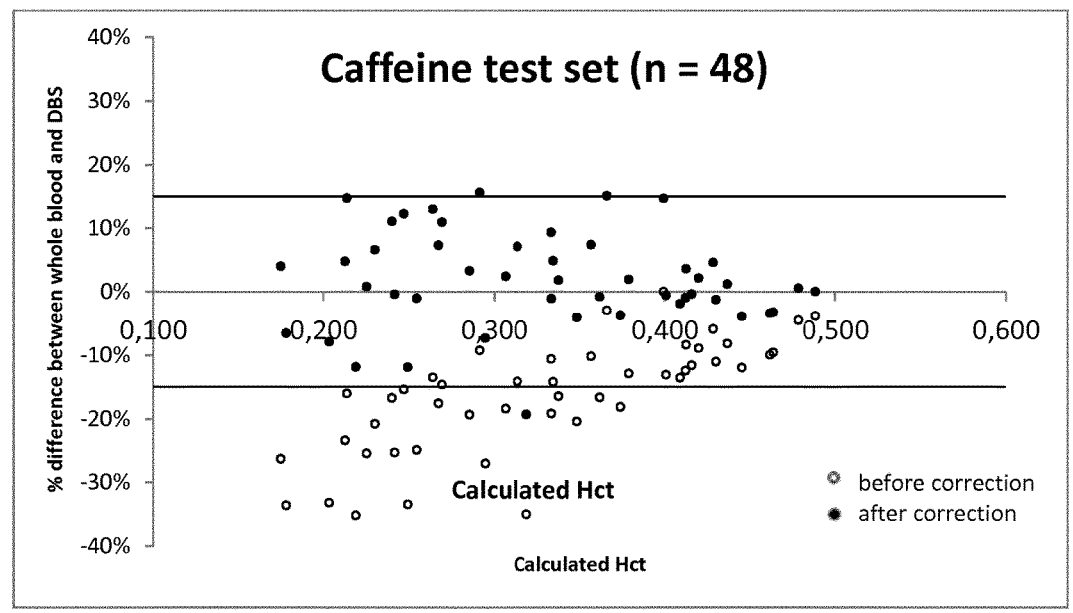
Figure 10C:
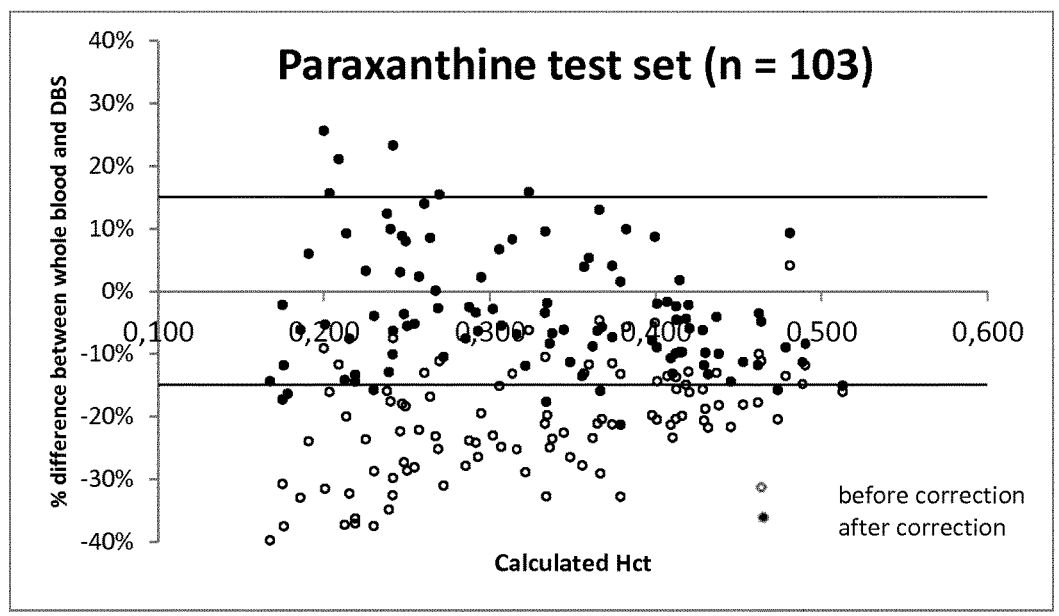

All patient samples were reanalysed three days after the original analysis and none of the samples deviated more than ±5% from the average of both analyses, demonstrating the excellent reproducibility of the method (see FIG. 9).

The invention claimed is:

1. A non-destructive method of estimating hematocrit (Hct) of whole blood from a dried blood sample prepared from the whole blood, the method comprising:
   a) determining the total amount of hemoglobin derivatives comprising oxyhemoglobin, met-hemoglobin and hemichrome in a dried blood sample,
      wherein the total amount of said hemoglobin derivatives in a dried blood sample is determined by measuring the reflectance, absorbance, or transmittance of the dried blood sample at the quasi-isosbestic point of said hemoglobin derivatives, or
      wherein the total amount of said hemoglobin derivatives in a dried blood sample is determined by calculating the sum of the amounts of each of oxyhemoglobin, met-hemoglobin and hemichrome, wherein the amount of each of oxyhemoglobin, met-hemoglobin and hemichrome is determined by measuring the reflectance, absorbance, or transmittance of the dried blood sample at multiple wavelengths, and comparing the measured spectrum with reference spectra of the respective hemoglobin derivatives; and
   b) estimating the hematocrit from the total amount of said hemoglobin derivatives, wherein the hematocrit is estimated using a calibration curve providing a correlation between hematocrit and the total amount of said hemoglobin derivatives in a dried blood sample.

2. The method according to claim 1, wherein comparing the measured spectrum with reference spectra of said respective hemoglobin derivatives is performed by means of a light transport model and/or using a least square fitting procedure.

3. The method according to claim 1, wherein the quasi-isosbestic point of said hemoglobin derivatives is set between 585 and 595 nm, preferably between 587 and 591 nm, more preferably between 588 and 590 nm, and most preferably at about 589 nm.

4. The method according to claim 1, wherein the reflectance, absorbance, or transmittance of the dried blood sample at multiple wavelengths is measured at wavelengths lying within 500 to 700 nm or encompassing the 500 to 700 nm range.

5. The method according to claim 1, wherein said method is performed via non-contact diffuse reflectance spectroscopy, preferably using an optical reflectance probe, a multispectral, or hyperspectral camera.

6. The method according to claim 1, wherein additionally the reflectance, absorbance, or transmittance of carboxyhemoglobin and/or sulfhemoglobin is used to estimate the Hct.

7. The method according to claim 1, wherein the calibration curve is established by determining the total amount of said hemoglobin derivatives in dried blood samples prepared from calibration samples, such as (whole) blood samples, with a known hematocrit, and plotting the total amount of said hemoglobin derivatives against the known hematocrit.

8. The method according to claim 1, further comprising the use of calibration curves of blood with a mean corpuscular hemoglobin concentration (MCHC) that corresponds to the average of the target population.

9. The method according to claim 1, wherein said dried blood sample is selected from the group comprising: dried blood spots, dried matrix samples, dried matrix microsamples, volumetric dried blood samples, and other dried blood samples.

10. A system for estimating the Hct in a dried blood sample, comprising:
    a means for measuring the reflectance, absorbance or transmittance of a dried blood sample at a wavelength ranging at least from 500 to 700 nm or at a wavelength of 589 nm (+/−5 nm); and
    a computer implemented program for calculating the Hct from the measurement, using the method according to claim 1.

11. The system according to claim 10, which is integrated in a dried blood sample analyser.

12. The system according to claim 11, wherein said dried blood sample analyser uses on-line elution or desorption technology, automated extraction or punched disc extraction or wherein said dried blood sample analyser is an automated volumetric absorptive microsampling analyser, or a spectrometric dried blood sample scanning system.

13. The system according to claim 10, wherein said means for measuring the reflectance, absorbance or transmittance of a dried blood sample is a means for performing non-contact diffuse reflectance spectroscopy at a wavelength ranging at least from 500 to 700 nm, or at a wavelength of 589 nm (+/−5 nm).

14. The system according to claim 10, wherein said means for performing non-contact diffuse reflectance spectroscopy comprises a light source, a light guiding means, and a spectral detection means.

15. The system according to claim 14, wherein said means for performing non-contact diffuse reflectance spectroscopy further comprises a spectral filter between said light guiding means and said spectral detection means.

16. The system according to claim 15, wherein said spectral filter is selected from the group of tunable or random access filters.

17. The system according to claim 14 wherein said spectral detection means is selected from: a spectrograph; a photodetector; an optical reflectance/backscatter probe system; or a spectral camera such as a staredown camera, a multispectral or hyperspectral imaging camera or a CCD camera.

18. The system according to claim 14, wherein said light source is capable of emitting light of a wavelength set between at least 500 and 700 nm, preferably wherein said light source is a halogen or LED light source.

19. The system according to claim 10, wherein said means for performing non-contact diffuse reflectance spectroscopy further comprises a computer controlling the light source and collecting the reflectance or transmittance data.

20. The system according to claim 10, further comprising a dried blood sample sampler, preferably an autosampler.

21. The system according to claim 20, wherein said dried blood sample sampler is selected from the group comprising: on-line elution or desorption, automated extraction, automated volumetric absorptive microsampling extraction, punched disc extraction, or spectrophotometric dried blood spot scanning systems.

* * * * *